United States Patent [19]
Viret

[11] Patent Number: 4,593,107
[45] Date of Patent: Jun. 3, 1986

[54] 5-ACETYLOXY-L-TRYPTOPHANE AND PREPARATION METHOD THEREOF

[76] Inventor: Jacques Viret, 89 B, Route de Florissant, Geneve, Switzerland, 1206

[21] Appl. No.: 653,057

[22] Filed: Sep. 21, 1984

Related U.S. Application Data

[63] Continuation of Ser. No. 508,563, Jun. 28, 1982, abandoned, which is a continuation of Ser. No. 345,736, Feb. 4, 1982, abandoned.

[30] Foreign Application Priority Data

Feb. 4, 1981 [FR] France ................... 81 02172

[51] Int. Cl.⁴ ........................................... C07D 209/20
[52] U.S. Cl. ................................................... 548/496
[58] Field of Search .......................... 548/496; 514/419

[56] References Cited

U.S. PATENT DOCUMENTS 3,075,993 11/1963 Chemerda ..................... 548/496

FOREIGN PATENT DOCUMENTS 121161 12/1966 Czechoslovakia .
1457260 9/1961 France .
2001309 1/1977 France .
2395995 1/1979 France .

OTHER PUBLICATIONS

Chemical Abstracts, vol. 54, No. 16, Aug. 25, 1960, col. 17725H.
Courvoisier et al, "Proced. Intern. Cong. Neuro-Pharm. 1st, Rome, pp. 303-307 (1958).

Primary Examiner—Glennon H. Hollrah
Assistant Examiner—D. B. Springer
Attorney, Agent, or Firm—Arnold, White & Durkee

[57] ABSTRACT

The present invention relates to 5-acetyloxy-L-tryptophane and its addition salts, as novel industrial products.

The invention further relates to a method for the preparation of 5-acetyloxy-L-tryptophane and of its salts by O-acetylation of 5-hydroxy-L-tryptophane.

The compounds according to the invention are found to be therapeutically useful, in particular in neuropsychiatry.

4 Claims, 2 Drawing Figures

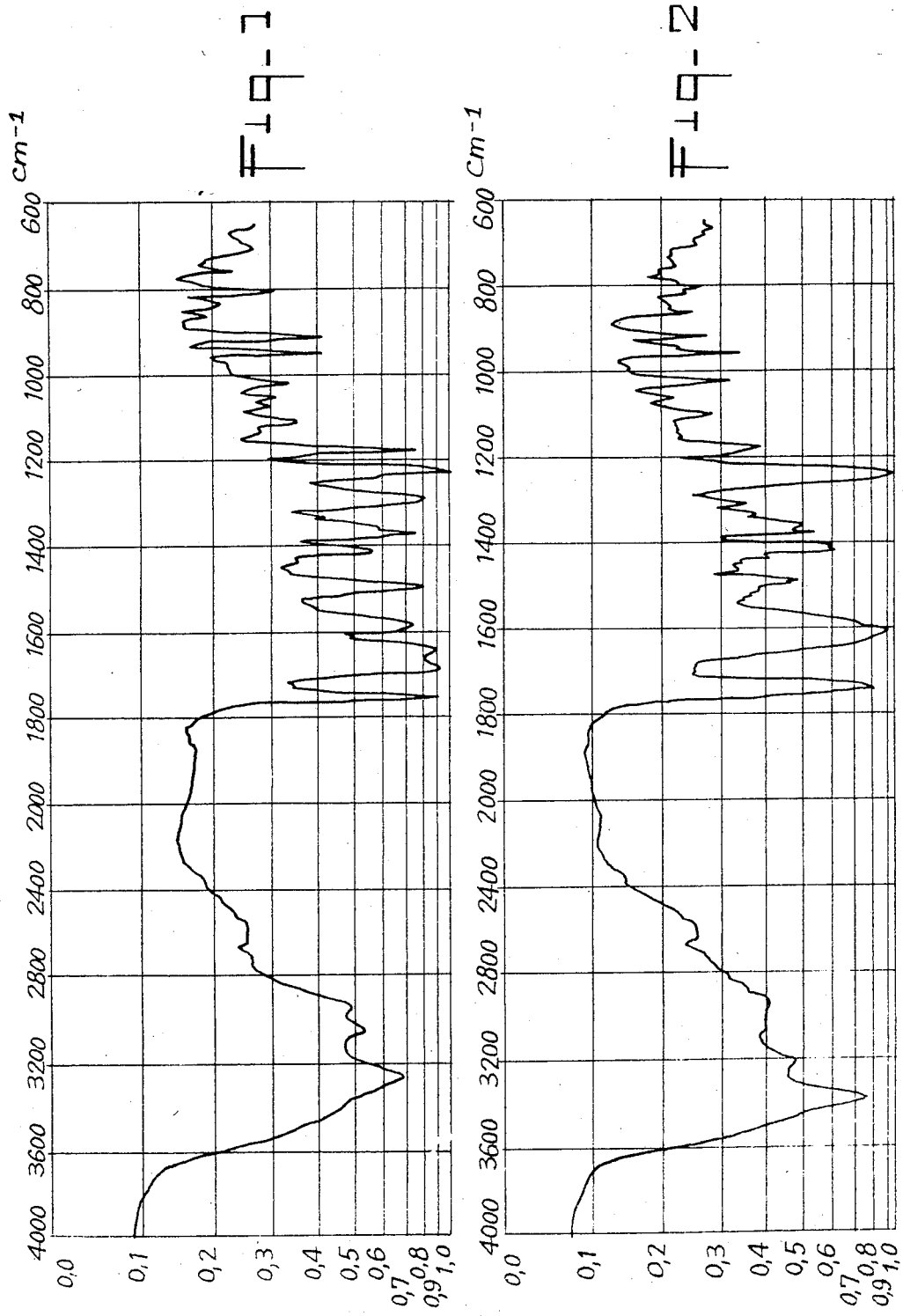

5-ACETYLOXY-L-TRYPTOPHANE AND PREPARATION METHOD THEREOF

This is a continuation application of Ser. No. 508,563, filed June 28, 1983, now abandoned which was a continuation of Ser. No. 345,736 filed Feb. 4, 1982, now abandoned.

The present invention relates to 5-acetyloxy-L-tryptophane and its addition salts as novel industrial products. It further relates to the method for the preparation of said products and their therapeutical use, and particularly in neuropsychiatry.

The preparation of 5-acetyloxy-L-tryptophane and of its addition salts has never been described until now.

It is known that W. SAKAMI and G. TOENNIES, J. Biol. Chem., 144, 203 (1942) have proposed a method for acetylating the alcohol functions of hydroxyaminoacids, and that said method has been applied with success for the O-acetylation of L-hydroxyproline, of DL-serine, of DL-threonine and of L-tyrosine, but that it could never be applied to the O-acetylation of an hydroxyindoleamino acid such as hydroxytryptophane. This is explained by the fact that one of the co-authors of the aforesaid article [see to this effect G. GOENNIES and J. J. KOLB, J. Biol. Chem., 144, 219 (1942)] claims to have observed that acetylation takes place on the indole nitrogen atom.

The O-acetylation according to the invention is also different from the N-acetylation of the $NH_2$ group of 5-hydroxy-L-tryptophane which is especially illustrated in French Patent No. 71-37901 (published under No. 2 113 077).

The present invention proposes an O-acetylation method permitting to obtain 5-acetyloxy-L-tryptophane and its addition salts. And since 5-acetyloxy-L-tryptophane an its addition salts have proved therapeutically useful, in particular in neuropsychiatry, the invention further proposes a pharmaceutical composition which contains, in association with a physiologically acceptable excipient, at least one compound selected from the group constituted by 5-acetyloxy-L-tryptophane and its addition salts.

The invention therefore relates, as novel industrial product, to a 5-hydroxytryptophane derivative which is characterized in that it is selected from the group consisting of:

(a) 5-acetyloxy-L-tryptophane, and
(b) its addition salts.

The invention further relates to a method for the preparation of 5-acetyloxy-L-tryptophane from 5-hydroxy-L-tryptophane, which method consists in reacting an equivalent of 5-hydroxy-L-tryptophane with an equivalent of perchloric acid in solution in anhydrous acetic acid, in treating an equivalent of the resulting salified product with 1 or 2 equivalents (2 preferably) of acetic anhydride to obtain 5-acetyloxy-L-tryptophane acetate, the neutralization of this acid addition salt, in particular with $NH_4OH$ giving 5-acetyloxy-L-tryptophane. The other addition salts can be obtained according to a method known per se, from 5-acetyloxy-L-tryptophane, and preferably by reacting 5-acetyloxy-L-tryptophane with an inorganic acid (such as for example HCl, HBr, $H_2SO_4$, $HNO_3$), or an organic acid (such as HCOOH, $CH_3CH_2COOH$ $C_6H_5COOH$, or else oxalic, fumaric, maleic, malic, ascorbic, p-toluenesulphonic, methanesulphonic and tartric acids). It is also possible according to the invention to prepare quaternary ammonium type addition salts by reacting 5-acetyloxy-L-tryptophane with for example $ICH_3$ or $ClCH_3$.

The method according to the invention can also be used with 5-hydroxy-DL-tryptophane as starting compound. In this case, acetate of 5-acetyloxy-DL-tryptophane then 5-acetyloxy-DL-tryptophane are obtained, the L isomers of these compounds being later isolated if necessary according to a method known per se.

The invention will be more readily understood on reading the following examples of preparation given by way of illustration and non-restrictively.

EXAMPLE 1

Acetate of 5-acetyloxy-L-tryptophane monohydrate

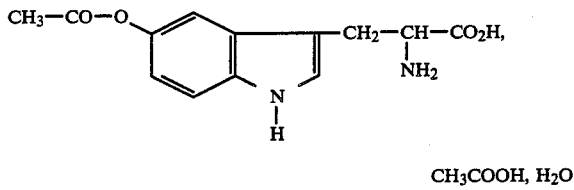

$CH_3COOH, H_2O$ 25 g of 5-hydroxy-L-tryptophane (0.114 mole) are dissolved in 1140 ml of a solution 0.1N of perchloric acid in glacial acetic acid (entirely free of water), contained in a 2-liter balloon flask.

114 ml of a solution at 20% (W/v) of acetic anhydride (0.22 mole) in acetic acid are added dropwise.

The mixture is brought to 50° C. and kept at that temperature for 15 minutes.

23 ml of water are added and the mixture is left to react at 50° C. for 5 minutes.

It is then cooled down to room temperature (15°–20° C.).

45 ml of an aqueous solution at 40% (w/v) of cyclohexylamine are added.

then 1.14 l of diisopropyl ether are poured dropwise in the acetic solution (in which the product has already begun to crystallize).

After what, the resulting mixture is stirred for 1.5 hours.

It is then filtered, rinsed first with 180 ml of an acetic acid-diisopropyl ether (50:50) v/v mixture, and then with 50 ml of diisopropyl ether, Finally it is dried under phosphorous vacuum.

32.3 g of raw 5-acetyloxy-L-tryptophane mononhydrate acetate are obtained (yield: 83.7%);

Purification is achieved as follows:

32.3 g of the raw product are placed in suspension in 120 ml of a water-ethanol (50:50) v/v mixture contained in a 200 ml Erlenmeyer flask. The resulting mixture is brought for 5 minutes to the reflux temperature, and then cooled down to room temperature (15°–20° C.). It is stirred for two hours at 20° C. and left to stand for one night at 5° C. After what, it is filtered and rinsed with 2×30 ml of a water-ethanol (50:50) v/v mixture, and then dried under phosphorous vacuum.

28.2 g of purified acetate of 5-acetyloxy-L-tryptophane monohydrate are thus obtained (yield: 87.3%). The melting point (determined according to the method known as the capillary tube method) is of about 225° C.

The presence of one molecule of water in the purified final product is checked by K. FISCHER's titrimetric method.

The monohydrated salt is in the form of a white or nearly white powder, which is odorless or nearly odorless, non-hygroscopic in an atmosphere of 50° of relative humidity.

Said salt is soluble in water: a solution at 1% w/v is obtained at room temperature, but a solution at 2% can only be obtained under heat (in water bath at 60° C.), this last solution remaining however whole when returned to normal temperature.

This salt is virtually insoluble in anhydrous ethanol, even once the solvent has been brought to the boil.

A solution at 1% w/v cannot be completely achieved in a mixture of water and ethanol (50:50) v/v at room temperature, but it becomes possible with a heating in a water bath at 60° C. and remains whole when returned to normal temperature.

The absorption spectrum IR (see FIG. 1: absorbance in ordinate and $cm^{-1}$ in abscissa) shows the following characteristic bands: 1750 $cm^{-1}$ (carbonyl ester), 1680 $cm^{-1}$ (carboxylic acid) and 1635 $cm^{-1}$ (carboxylate).

The rotary power of the product of Example 1 in solution at 2% in HCl 2N is $\alpha_D^{20} = +8°$.

EXAMPLE 2

5-acetyloxy-L-tryptophane

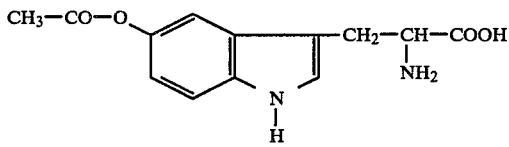

28.19 g of acetate of 5-acetyloxy-L-tryptophane monohydrate (purified as indicated in Example 1) are placed in suspension in 750 ml of water contained in a 1-liter beaker.

6.7 ml of an aqueous solution of ammonia at 20.9% (density: 70%) are added. A dissolution is observed followed by the formation of a thick precipitate.

The whole is stirred for three hours at 20° C.,

Then it is filtered and rinsed in 2×30 ml of water.

15.2 g of 5-acetyloxy-L-tryptophane are thus obtained (Yield: 70%). The melting point (determined according to the capillary tube method) is of about 220° C.

This product is in the form of a white or nearly white powder, odorless or nearly odorless, and non-hydroscopic in an atmosphere of 70° of relative humidity.

It is soluble in water but under heat for concentrations at 1% as well as for concentrations at 2% w/v (in a water bath at 60° C.), both these solutions remaining whole when returned to normal temperature.

The absorption spectrum IR (see FIG. 2: absorbance in ordinate and $cm^{-1}$ in abscissa) shows the following characteristic bands: 1735 $cm^{-1}$ (carbonyl ester) and 1605 $cm^{-1}$ (carboxylate).

The rotary power of the product of Example 2 in solution in HCl 2N is $\alpha_D^{20} = +9°$.

The results of the pharmacological tests conducted are given hereunder.

| TOXICITY |
|---|
| (1) Intraperitoneal administration to 10 male mice: 5-acetyloxy-L-tryptophane administered in doses of 800 mg/kg. |
| 1 hour after administration: 2 dead out of 10. |
| 24 hours after administration: 2 dead out of 8. |
| Total over 10 days: 4 dead out of 10. |
| The product of Example 1 administered in doses of 800 mg/kg to 10 male mice. |
| 1 hour after administration: no dead. |
| 24 hours after adinistration: 1 dead. |
| The following days: no dead. |
| Total: one dead out of 10. |
| (2) Oral administration to 10 male mice: 5-acetyloxy-L-tryptophane administered in doses of 1 g/kg. |
| 1 hour after administration: 2 dead. |
| 24 hours after administration: no dead. |
| 10 days after administration: no dead. |
| Total: 2 dead out of 10 within one hour following administration. |
| The product of Example 1 administered in doses of 1 g/kg. |
| Total, no dead within the following hours and 10 days. |

PHARMACOLOGY

The discovery in the animal of characteristic motor manifestations after the administration of 5-hydroxy-L-tryptophane in sufficient dose, has already been the subject of many works. These manifestations are attributed to an activation of the cerebral serotoninergic receptors in animals pretreated with IMAO.

In the experimental conditions adopted herein, the 5-acetyloxy-L-tryptophane as well as the product of Example 1 cause alterations of the motor behaviour in mice, which are more important than those caused by an equimolecular dose of 5-hydroxy-L-tryptophane.

The pharmacological research which has been conducted leads one to think that the cerebral concentration in serotonin is faster and greater after the administration of 5-acetyloxy-L-tryptophane and of its salts than after the administration of 5-hydroxy-L-tryptophane.

The clinical applications deriving from the pharmacological discoveries concern the serotonin deficiencies which are the cause of neuropsychiatric disorders such as:

dysthymia, and in particular depressive syndromes (with possible association of anti-depressants);
sleeplessness (inducing effect),
certain abnormal movements.

Average posology recommended in humans is of the order of 1.5 to 2 g by oral route and 0.5 g by parenteral route, of 5-acetyloxy-L-tryptophane or of one of its addition salts daily.

What is claimed is:

1. A compound which is 5-acetyloxy-L-tryptophane or its pharmaceutically acceptable acid addition salts.

2. The compound of claim 1 which is 5-acetyloxy-L-tryptophane.

3. The compound of claim 1 which is the mono acetate salt of 5-acetyloxy-L-tryptophane monohydrate.

4. A method of preparing 5-acetyloxy-L-tryptophane from 5-hydroxy-L-tryptophane comprising the steps of:
   (a) reacting 5-hydroxy-L-tryptophane with perchloric acid in solution in anhydrous acetic acid;
   (b) treating an equivalent of the resulting product with at least 1 equivalent of acetic anhydride to obtain 5-acetyloxy-L-tryptophane acetate; and
   (c) neutralizing the 5-acetyloxy-L-tryptophane acetate with ammonium hydroxide to obtain 5-acetyloxy-L-tryptophane.

* * * * *

UNITED STATES PATENT AND TRADEMARK OFFICE
CERTIFICATE OF CORRECTION

PATENT NO. : 4,593,107

DATED : June 3, 1986

INVENTOR(S) : Jacques Viret

It is certified that error appears in the above-identified patent and that said Letters Patent are hereby corrected as shown below:

Page 1, under Related U.S. Application Data, that portion reading "Jun. 28, 1982" should read --Jun. 28, 1983--.

Signed and Sealed this

Twenty-fifth Day of November, 1986

Attest:

DONALD J. QUIGG

*Attesting Officer*     *Commissioner of Patents and Trademarks*